(12) United States Patent
Moorcroft et al.

(10) Patent No.: US 8,080,016 B2
(45) Date of Patent: Dec. 20, 2011

(54) WIRE RETAINER FOR SURGICAL DEVICE

(75) Inventors: Christopher Ian Moorcroft, Staffordshire (GB); Peter Jan Ogrodnik, Staffordshire (GB); Peter Brian Macfarlane Thomas, Staffordshire (GB)

(73) Assignee: Intelligent Orthopaedics Limited, Stoke On Trent (GB)

( * ) Notice: Subject to any disclaimer, the term of this patent is extended or adjusted under 35 U.S.C. 154(b) by 834 days.

(21) Appl. No.: 11/995,668

(22) PCT Filed: Jul. 3, 2006

(86) PCT No.: PCT/GB2006/002464
§ 371 (c)(1), (2), (4) Date: Jul. 7, 2008

(87) PCT Pub. No.: WO2007/010185
PCT Pub. Date: Jan. 25, 2007

(65) Prior Publication Data
US 2008/0300606 A1  Dec. 4, 2008

(30) Foreign Application Priority Data
Jul. 20, 2005  (GB) ................. 0514881.2

(51) Int. Cl.
*A61B 17/58* (2006.01)
*A61B 17/56* (2006.01)
(52) U.S. Cl. ........................ 606/103; 606/60

(58) Field of Classification Search .............. 606/54–60, 606/103; 403/3, 4
See application file for complete search history.

(56) References Cited

U.S. PATENT DOCUMENTS

| 4,195,401 A | | 4/1980 | Galloup | |
|---|---|---|---|---|
| 4,982,932 A | * | 1/1991 | Baker | ............................. 256/47 |
| 5,496,319 A | * | 3/1996 | Allard et al. | ..................... 606/56 |
| 5,779,703 A | * | 7/1998 | Benoist | ........................... 606/54 |

FOREIGN PATENT DOCUMENTS
DE  8627450  2/1987

OTHER PUBLICATIONS

International Search Report prepared by the European Patent Office on Oct. 13, 2006 for PCT/GB2006/002464; Applicant, Intelligent Orthopaedics Ltd.
International Preliminary Report on Patentability for International PCT Patent Application No. PCT/GB 2006/002464, issued Jan. 22, 2008.

* cited by examiner

*Primary Examiner* — Pedro Philogene
(74) *Attorney, Agent, or Firm* — Sheridan Ross P.C.

(57) ABSTRACT

A wire retainer (10) for securing wire under tension comprising a body (11) having an exterior surface and a far end (11a) and a near end (11b) and a bore (12) extending therebetween in the general direction of a first axis (X) in a first plane (XY), the bore receiving an end of the wire (3) in use, a first slot (13) substantially in said first plane and having a far end which coincides with the far end of the body and a near end intermediate the far and near ends of the body, the first slot extending between said bore and said exterior surface and a second slot (14) intersecting said first slot at the near end thereof and at said bore.

13 Claims, 3 Drawing Sheets

WIRE RETAINER FOR SURGICAL DEVICE

CROSS REFERENCE TO RELATED APPLICATION

This application is a national stage application under 35 U.S.C. 371 of PCT Application No. PCT/GB2006/002464 having an international filing date of Jul. 3, 2006, which designated the United States, which PCT application claimed the benefit of United Kingdom Application Serial No. 0514881.2, filed Jul. 20, 2005, the entire disclosure of each of which is hereby incorporated herein by reference.

This invention relates to the field of retainers for retaining wire associated with surgical devices, in particular wire associated with orthopaedic surgical devices such as bone fixators for the treatment of fractured bones.

BACKGROUND

Bone is capable of self-healing at a fracture site by the formation of callus which is able to reunite the ends of the fractured bone. Callus formation is triggered and maintained by relative movement of the fractured bone ends and occurs during a specific and limited time period following occurrence of the fracture.

If allowed to heal completely naturally, a fractured bone would heal in a poorly aligned condition, resulting in consequential future problems. Therefore the fractured bone ends are more usually manipulated into a well-aligned condition (fracture reduction) before callus formation and the natural healing process occurs. Once reduced, the fracture needs to be supported or fixed in order to maintain the desired alignment.

Rigid fixation of the fractured bone ends means that they are kept well aligned but may lead to a reduction or prevention of the formation of callus, therefore prolonging the natural healing process.

Treatment of a bone fracture by providing external support (e.g. a plaster of Paris cast) allows relative movement of the fractured bone ends to occur, which promotes callus formation. However, such external supports may not be suitable to assist with the need to accurately align the fractured bone ends, particularly with unstable or metastable fractures.

To alleviate these problems, external bone fixators have been developed which hold the fractured bone ends together sufficiently rigidly to maintain accurate alignment and yet at the same time allow sufficient relative movement between the fractured bone ends to promote callus formation. Such external fixators are applied externally to the injured limb and are attached to the fractured bone ends by bone pins or screws which pass through the soft tissue of the limb and into the bone.

A means for securing wires to a fixator is described in U.S. Pat. No. 4,978,348 (Ilizarov) wherein wires or fixing pins are secured in wire holders which consist of a bolt with plates mounted thereon and open slots in which the wires of fixing pins locate for clamping in a criss-cross manner.

An example of a ring fixator is described in WO99/60950 (Electro-Biology, Inc). This document discloses a ring-shaped external fixator which secures one or more tension wires adapted to pass through the bone. The tension wires are secured by means of an adjustable tension wire carriage of relatively complex construction.

In some cases, the end of the tension wire needs to be secured at an angle to the plane containing the ring. In such cases, articulated (and hence relatively complex) clamping elements are required. U.S. Pat. No. 6,537,275 (Orthofix Srl) discloses a simplified clamping element for securing tension wires ("bone fragment stretching wires") to the rings of a fixator. The clamp element includes a swivel joint to enable the desired angular position to be selected. The tension wire is threaded through a hole in the clamping element and held therein by means of a grub screw which moves perpendicular to the longitudinal axis of the wire to clamp down thereon. This grub screw clamping arrangement is a well-known means of securing tension wires, not only used in the articulated clamping element of U.S. Pat. No. 6,537,275.

Tension wires are not only used in fixators of the types described above, but also in surgical orthopaedic reduction apparatus such as that described in EP0984729 (Keele University et al). The invention described herein may also be useful in any surgical applications in which tension wires need to be secured or retained.

SUMMARY OF THE INVENTION

According to the present invention there is provided a surgical apparatus comprising a wire retainer for securing wire under tension, said retainer comprising a body having an exterior surface and a far end and a near end and a bore extending therebetween in the general direction of a first axis in a first plane, the bore receiving an end of the wire in use, a first slot substantially in said first plane and having a far end which coincides with the far end of the body and a near end intermediate the far and near ends of the body, the first slot extending between said bore and said exterior surface and a second slot intersecting said first slot at the near end thereof and at said bore.

In a preferred embodiment, relative movement between said body and the end of the wire moves the end of the wire into said second slot such that the end of the wire is secured in a position that is substantially out of said first plane.

Preferably, said relative movement is caused by bending the end of the wire into said second slot. Alternatively, said relative movement is caused by rotation of said body about said first axis.

In a preferred form, said retainer is part of an orthopaedic fixator or is part of surgical orthopaedic reduction apparatus.

Preferably, said second slot is in a plane which is substantially orthogonal to said first plane.

Preferably, the secured position of the wire is substantially orthogonal to said first axis.

In a preferred form, the retainer further comprises locking means for preventing relative movement between the wire and the body, when the end of the wire is in the secured position.

Preferably, said body is generally cylindrical and/or said near end of said body has a narrowed diameter.

Preferably, the body is made from any suitable material, for example stainless steel, titanium or plastics.

In a preferred form, said wire can be released from said secured position, in order to permit adjustment to the tension of the wire, and re-positioned in said secured position.

BRIEF DESCRIPTION OF THE DRAWINGS

Preferred embodiments of the present invention will now be more particularly described, by way of example only, with reference to the accompanying drawings wherein.

DETAILED DESCRIPTION

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith.

The terms "retain" and "retaining" are synonymous with the terms "secure" and "securing" and are used interchangeably therewith.

Figure 1:
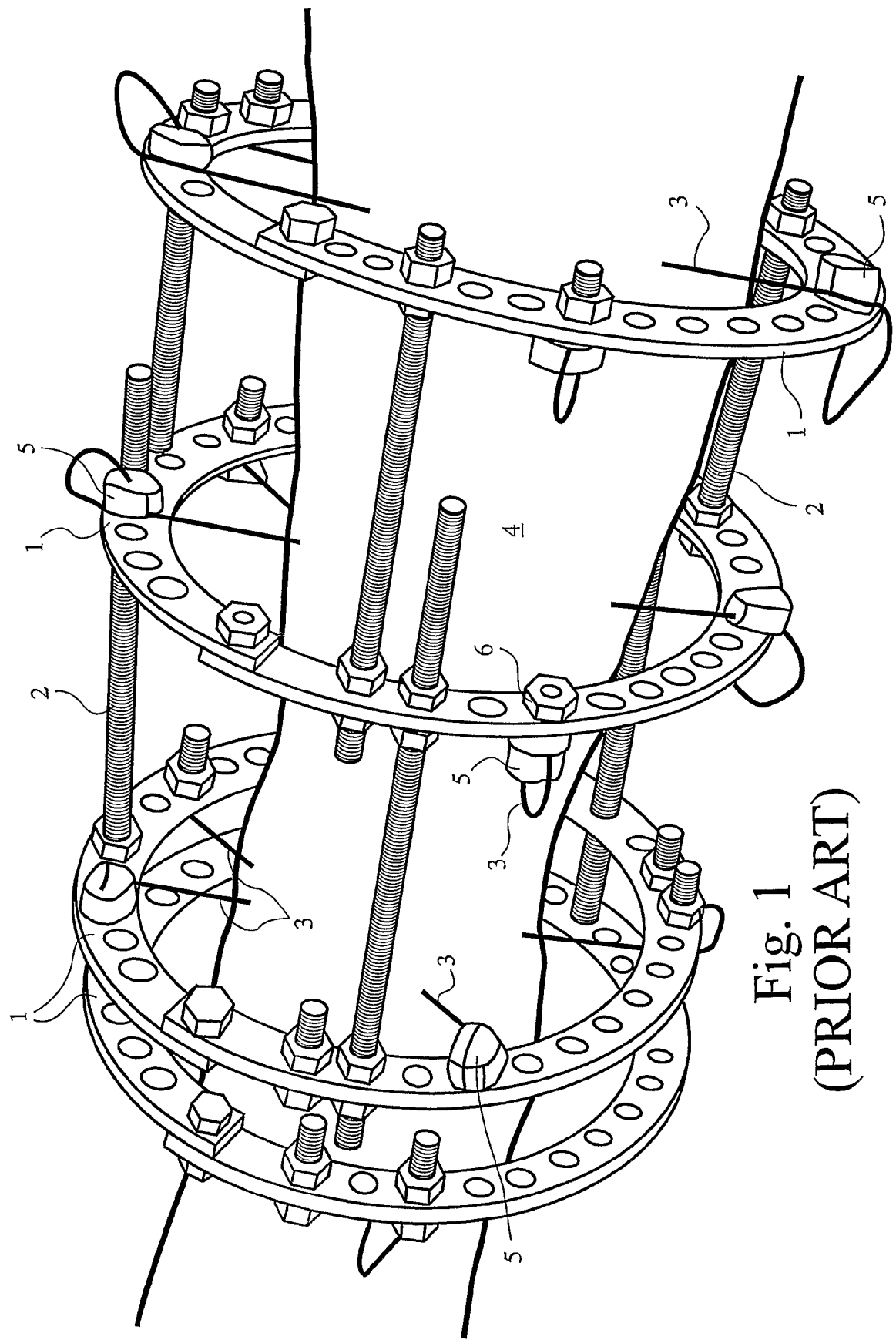
FIG. 1 is a perspective view of a ring fixator showing the location of tension wires and conventional wire retainers (PRIOR ART)

FIG. 1 shows a prior art ring fixator used in the treatment of fractured bones. The fixator comprises a number of metal rings 1, rigidly connected together by means of screw-threaded bolts 2. The fixator is provided with a number of tension wires 3. The tension wires enter the patient's leg 4 and are attached to the respective parts of the fractured bone. The wires 3 are attached under tension to the rings 1 by means of conventional wire retainers 5. Each wire retainer 5 grips the respective tension wire 3 by axially clamping the wire against the ring or against a part of the retainer by means of a grub screw or nut 6 which can be tightened accordingly. FIG. 1 is provided to illustrate an example context in which the wire retainer of the present invention can be used.

Figure 2:
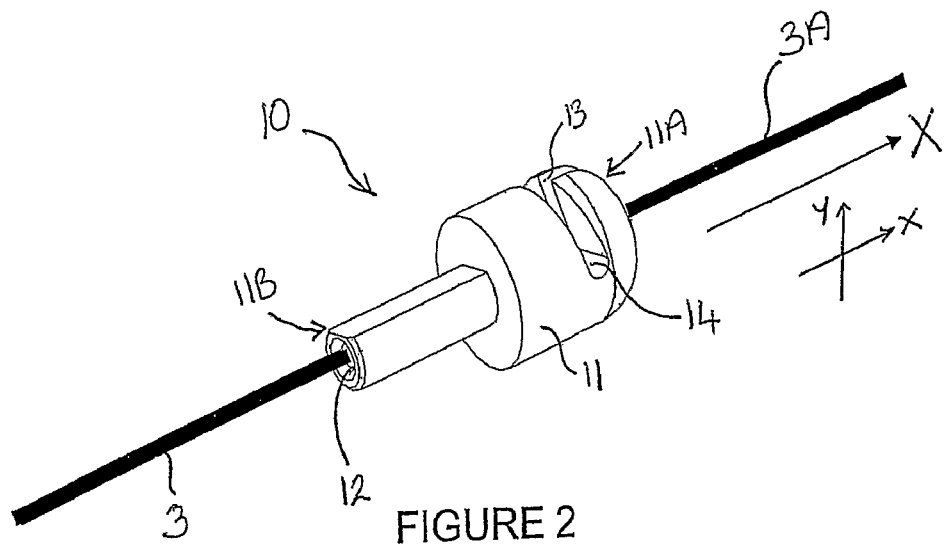
FIG. 2 is a perspective view of a wire retainer embodying the first aspect of the invention, showing the wire in the first stage of insertion.
Figure 3:
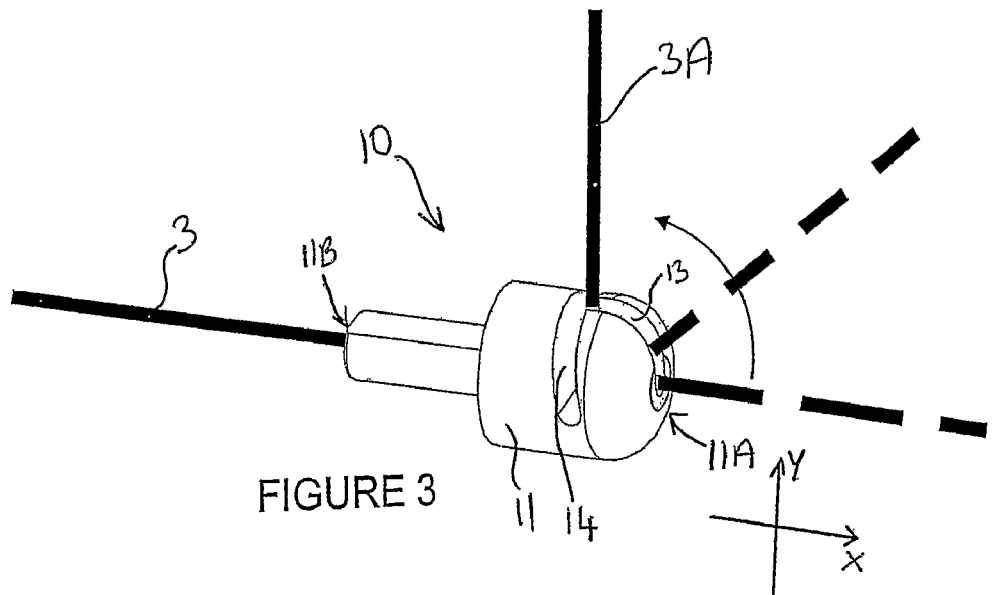
FIG. 3 is a perspective view of the wire retainer of FIG. 2, showing the wire in the second stage of insertion.
Figure 4:
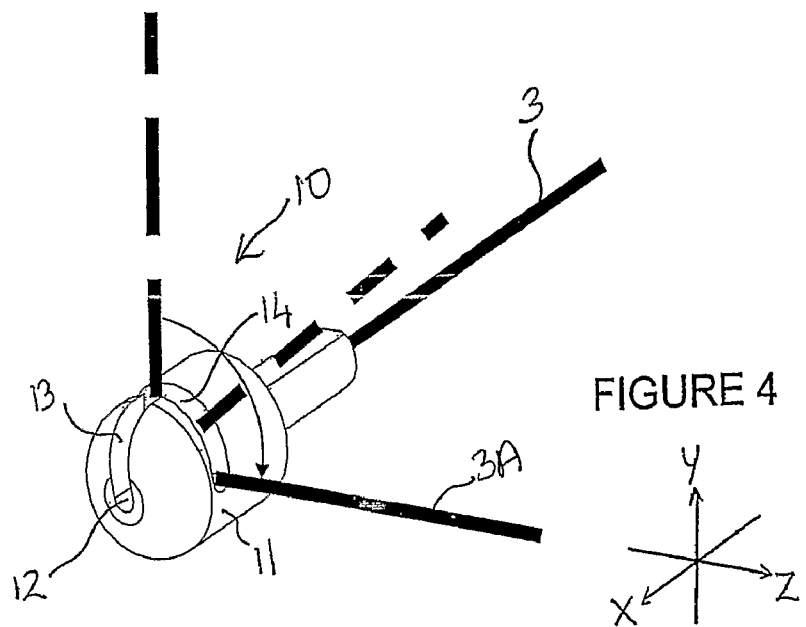
FIG. 4 is a perspective view of the wire retainer of FIG. 2, showing the wire in the third and final stage of insertion.

FIGS. 2-4 show the wire retainer of the present invention which can be used to replace the conventional wire retainers 5 illustrated in FIG. 1. The wire retainer 10 comprises a body 11 which is preferably generally cylindrical in shape. The body has a far end 11A and a near end 11B. The body preferably has a narrowed portion at near end 11B.

The terms "far" and "near" are used herein with respect to the patient. In other words, the "far end" 11A of the body 11 is that which, in use, is normally furthest from the patient and the "near end" 11B of the body 11 is that which is normally closest to the patient. These terms are not to be construed as limiting and are only used in order to facilitate the description of the invention.

The body 11 has a bore 12 extending between the far end 11A and the near end 11B. The bore extends in the general direction of a first axis X in a first plane XY and is of a suitable diameter to receive the end of a conventional tension wire 3.

At the far end of the body there is a first slot 13 substantially in said first plane XY which itself has a far end and a near end. The far end of slot 13 coincides with the far end 11A of the body and the near end of slot 13 is intermediate the far and near ends of the body. The first slot 13 extends between the bore 12 and the exterior surface of the body 11.

Intersecting the first slot 13 at the near end thereof is a second slot 14. The intersection of the two slots 13 and 14 also coincides with the bore 12.

Referring now to FIG. 2, it can be seen that the end 3A of a conventional tension wire 3 can be inserted through the body 11 via bore 12. In this first stage, illustrated in FIG. 2, the end of the wire 3A is generally in line with axis X and is located within plane XY.

Referring now to FIG. 3, the end of the wire 3A can be bent upwardly away from axis X, following slot 13 and still generally within plane XY, in the direction indicated by the arrow in FIG. 3, until the wire reaches the intersection between the two slots. In this second stage, illustrated in FIG. 3, the end of the wire 3A is generally orthogonal to axis X but is still located within plane XY.

Referring now to FIG. 4, the end of the wire 3A can be bent again, this time following the second slot 14 away from plane XY in the direction indicated by the arrow in FIG. 4. In this third stage, illustrated in FIG. 4, the end of the wire 3A is generally orthogonal to both axis X and plane XY. Preferably the end of the wire 3A ends up generally in plane XZ.

In this way, movement of the end of the wire into said second slot secures the wire in a position that is substantially out of plane XY so that subsequent relative movement between the body 11 and the wire 3A is prevented. In other words, the wire is held in the retainer 10 because the bending forces and friction between the wire and the slots and bore are sufficient to resist the tension in the wire (so that the wire is not pulled back through the bore of the body by said tension).

This provides a quick and convenient method of securing tension wires to a fixator or other orthopaedic surgical apparatus since no other fixings (grub screws, nuts or the like) are required. The reduction in the number of component parts reduces the likelihood of contamination and/or poor fit between the parts resulting from debris entering therein.

Furthermore, the tension in any particular wire can be easily adjusted by simply unbending the relevant wire, adjusting the tension and rebending the wire back into the secured position. This is of particular benefit in orthopaedic fixators where wire tension needs to be constantly monitored and adjusted.

Many alternative constructions of retainer using the principles described above can be envisaged. In one alternative embodiment, the relative movement between the body 11 and the wire 3A necessary in the third stage (FIG. 4) may be achieved by rotating the body 11 about axis X whilst keeping the wire 3A substantially stationary. In such an embodiment it is necessary to provide locking means in order to prevent unwanted subsequent rotation of the body once the desired tension has been set.

It is not necessary for wire 3A to be secured in plane XZ as illustrated in FIG. 4. Any position intermediate that shown in FIGS. 3 and 4 may serve to retain the wire in the retainer.

Figures 5, 6:
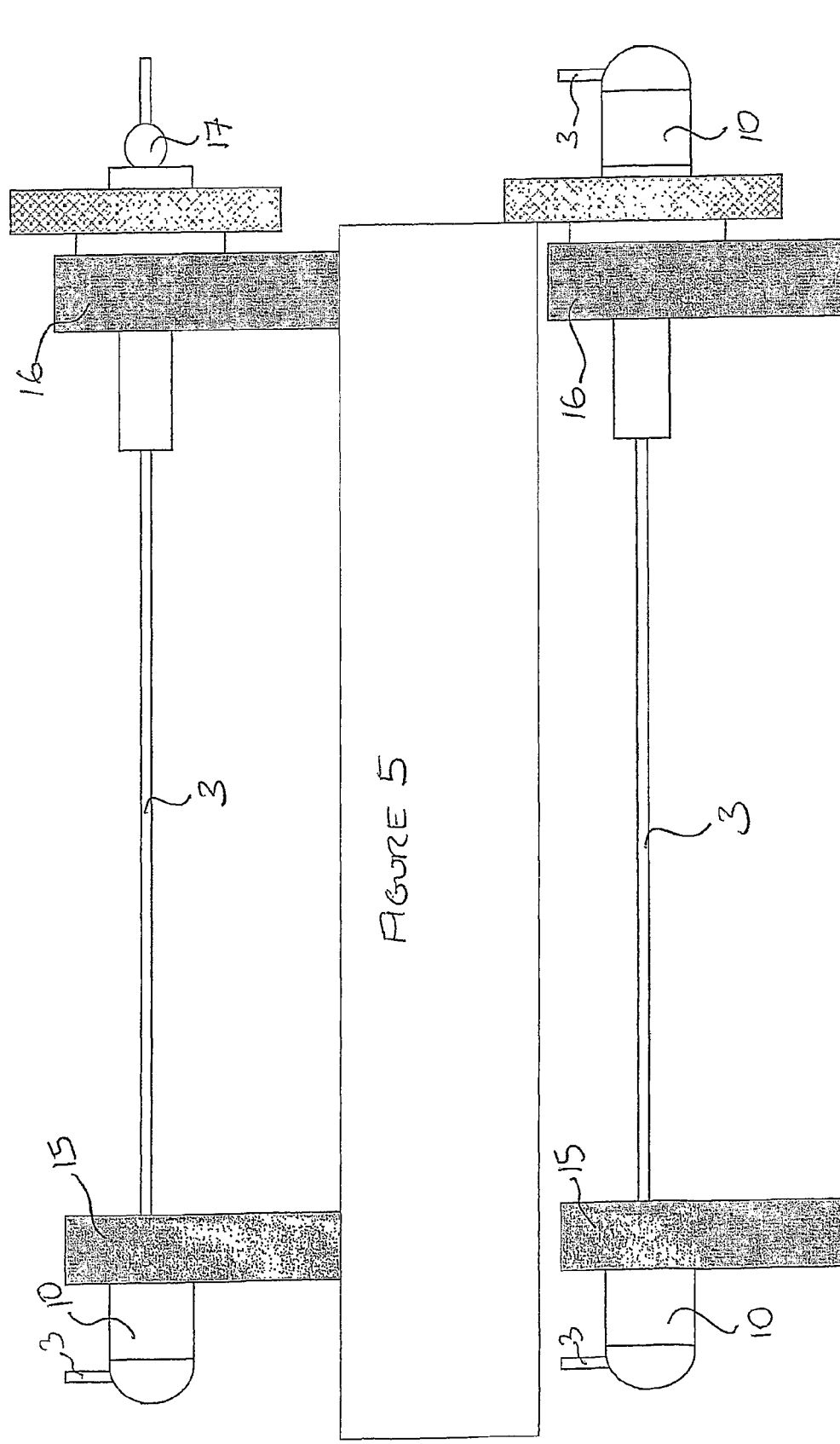
FIG. 5 is a side view of part of a surgical reduction machine including one of the FIG. 2 wire retainers.
FIG. 6 is a side view of part of a surgical reduction machine including two of the FIG. 2 wire retainers.

FIGS. 5 and 6 illustrate a further possible application of the wire retainer 10, this time in surgical orthopaedic reduction apparatus, used to reduce a fracture during surgery prior to applying a fixator. Suitable applications are any where tension needs to be selectively applied to a tension wire.

In FIG. 5, a tension wire 3 is illustrated which is fixed with respect to two supports 15, 16. At one support 16, the wire is fixed by means of a conventional olive arrangement 17. At the other support 15, the wire 3 is fixed by means of a retainer 10 as described above. FIG. 6 shows an alternative embodiment where the olive arrangement is replaced with another retainer 10 so there is a wire retainer 10 at both ends of wire 3.

Wherever a wire retainer 10 is used, it is easy and convenient to "undo" the wire, adjust tension as necessary, and then secure the wire in the retainer once again.

In a further embodiment (not illustrated), the olive arrangement is replaced with a collet which can be screwed and/or glued onto the end of the wire.

The invention claimed is:

1. A surgical apparatus comprising a wire retainer for securing wire under tension, said retainer comprising a body having an exterior surface and
   i. a far end and a near end and a bore extending therebetween in the general direction of a first axis in a first plane, the bore receiving an end of the wire in use,
   ii. a first slot substantially in said first plane and having a far end which coincides with the far end of the body and a near end intermediate the far and near ends of the body, the first slot extending between said bore and said exterior surface and
   iii. a second slot intersecting said first slot at the near end thereof and at said bore.

2. A surgical apparatus as claimed in claim 1 whereby relative movement between said body and the end of the wire moves the end of the wire into said second slot such that the end of the wire is secured in a position that is substantially out of said first plane.

3. A surgical apparatus as claimed in claim 1 wherein said relative movement is caused by bending the end of the wire into said second slot.

4. A surgical apparatus as claimed in claim 1 wherein said relative movement is caused by rotation of said body about said first axis.

5. A surgical apparatus as claimed in claim 1 wherein said retainer is part of an orthopaedic fixator.

6. A surgical apparatus as claimed in claim 1 wherein said retainer is part of surgical orthopaedic reduction apparatus.

7. A surgical apparatus as claimed in claim 1 wherein said second slot is in a plane which is substantially orthogonal to said first plane.

8. A surgical apparatus as claimed in claim 1 wherein the secured position of the wire is substantially orthogonal to said first axis.

9. A surgical apparatus as claimed in claim 1 further comprising locking means for preventing relative movement between the wire and the body, when the end of the wire is in the secured position.

10. A surgical apparatus as claimed in claim 1 wherein said body is generally cylindrical.

11. A surgical apparatus as claimed in claim 1 wherein said near end of said body has a narrowed diameter.

12. A surgical apparatus as claimed in claim 1 wherein the body is made from any suitable solid material, for example stainless steel, titanium or plastics.

13. A surgical apparatus as claimed in claim 1 wherein said wire can be released from said secured position, in order to permit adjustment to the tension of the wire, and re-positioned in said secured position.

* * * * *